US012414747B2

(12) United States Patent
Racette

(10) Patent No.: US 12,414,747 B2
(45) Date of Patent: Sep. 16, 2025

(54) PROTECTIVE COVER FOR C-ARM FLAT-PLATE DETECTOR

(71) Applicant: John William Racette, Roy, WA (US)

(72) Inventor: John William Racette, Roy, WA (US)

(*) Notice: Subject to any disclaimer, the term of this patent is extended or adjusted under 35 U.S.C. 154(b) by 224 days.

(21) Appl. No.: 18/351,118

(22) Filed: Jul. 12, 2023

(65) Prior Publication Data
US 2024/0023915 A1   Jan. 25, 2024

Related U.S. Application Data

(60) Provisional application No. 63/391,160, filed on Jul. 21, 2022.

(51) Int. Cl.
A61B 6/00   (2024.01)
(52) U.S. Cl.
CPC .................... A61B 6/4423 (2013.01)
(58) Field of Classification Search
CPC ..... A61B 6/107; A61B 6/4423; A61B 6/4441; A61B 6/4405
See application file for complete search history.

(56) References Cited

U.S. PATENT DOCUMENTS

| 4,447,060 | A | 5/1984 | Guinn | |
|---|---|---|---|---|
| 4,488,323 | A | 12/1984 | Colburn | |
| 4,498,615 | A | 2/1985 | Johnson | |
| 5,490,524 | A * | 2/1996 | Williams | A61B 46/10 128/853 |
| 6,715,917 | B1 | 4/2004 | Sohal et al. | |
| 7,044,132 | B2 | 5/2006 | Masini | |
| 7,108,422 | B2 * | 9/2006 | Borom | A61B 46/00 378/204 |
| 7,632,013 | B1 * | 12/2009 | Bueltmann | G03B 42/04 378/204 |
| 8,042,549 | B2 | 10/2011 | Kaska | |
| 8,225,495 | B2 | 7/2012 | Dehler | |
| 9,016,282 | B2 * | 4/2015 | Grajek | A01K 39/012 128/849 |
| 9,295,521 | B2 | 3/2016 | Pack et al. | |
| 9,855,178 | B2 * | 1/2018 | Rogers | A61B 46/10 |
| 10,149,731 | B2 * | 12/2018 | Adams | A61B 46/13 |
| 10,987,072 | B2 | 4/2021 | Goldberg | |
| 11,076,819 | B2 | 8/2021 | Belson et al. | |
| 11,246,549 | B2 | 2/2022 | Matthews | |

(Continued)

Primary Examiner — David J Makiya
Assistant Examiner — Soorena Kefayati
(74) Attorney, Agent, or Firm — Dunlap Bennett & Ludwig, PLLC; Anna L. Kinney

(57) ABSTRACT

A cover for a mini C-arm machine having a detector is designed to maintain a sterile field for a detector screen. The cover includes a panel having at least three integral sides, two being spaced-apart parallel to each other. The cover includes a pair of straps. One of the straps has an end portion fixed to one of the two parallel sides. The other strap has an end portion fixed to the other of the two parallel sides. The cover includes a hook-and-loop closure mechanism having a hooked portion and a looped portion. Each strap has a fixed end portion and a free, opposite end portion. The free end portion of one strap includes the hooked portion and the free end portion of the other strap includes the looped portion. Each closure portion is sized, when the closure portions are engaged, to retain the panel against the detector.

9 Claims, 4 Drawing Sheets

(56) References Cited

U.S. PATENT DOCUMENTS

| | | | |
|---|---|---|---|
| 11,331,057 B2 | 5/2022 | Stevens et al. | |
| 2003/0099325 A1* | 5/2003 | Galkin | A61B 6/0414 |
| | | | 378/37 |
| 2008/0216844 A1* | 9/2008 | Olfert | A61B 46/10 |
| | | | 128/856 |
| 2009/0316861 A1* | 12/2009 | Behle | G03B 42/04 |
| | | | 378/182 |
| 2010/0156318 A1 | 6/2010 | Quevedo | |
| 2012/0132217 A1* | 5/2012 | Rees | A61B 6/4423 |
| | | | 128/849 |
| 2013/0022175 A1* | 1/2013 | Abramovich | A61B 6/512 |
| | | | 378/189 |
| 2013/0025605 A1* | 1/2013 | Ball | A61B 46/10 |
| | | | 128/849 |
| 2013/0167845 A1* | 7/2013 | Grajek | A01K 39/012 |
| | | | 128/856 |
| 2014/0037070 A1* | 2/2014 | Noguchi | H10F 39/805 |
| | | | 378/189 |
| 2017/0066929 A1* | 3/2017 | Nariyuki | G01T 7/00 |
| 2019/0076104 A1* | 3/2019 | Rosink | A61B 6/06 |
| 2021/0228300 A1* | 7/2021 | DaCosta | A61B 5/0071 |
| 2022/0117566 A1* | 4/2022 | Yifat | A61B 6/107 |

* cited by examiner

PROTECTIVE COVER FOR C-ARM FLAT-PLATE DETECTOR

REFERENCE TO RELATED APPLICATION

The present nonprovisional patent application is based on U.S. provisional patent application Ser. No. 63/391,160 filed Jul. 21, 2022, hereby incorporated by reference in its entirety, for purposes of priority pursuant to Title 35, United States Code, Section 120.

FIELD OF THE INVENTION

The present subject matter is directed in general to a Complimentary Metal-Oxide Semiconductor (CMOS) detector equipped with a so-called C-arm and more particularly is directed to a CMOS detector having a flat plate adapted and configured for providing the detector with a sterile field for instruments.

BACKGROUND OF THE INVENTION

Low-dose CMOS detectors equipped with scalable multi-camera systems having embedded image-processing software designed for medical applications are becoming more frequently used in connection with certain medical office visits. Certain such CMOS detectors include an arm that is movable (preferably vertically and horizontally) and has a "C"-shaped distal-end portion adapted and configured to securely retain a plate designed to hold an assortment of medical instruments in a sterile field until needed by a medical practitioner for a procedure upon a patient.

Current plate coverings, after being ripped, perforated, or otherwise compromised during a medical procedure, generally breach a sterile field, cause a delay in the medical procedure, and raise concerns involving risk of infection.

U.S. Pat. No. 10,987,072 to Goldberg discloses a sterile X-ray imaging C-arm cover which includes an enclosure configured to be secured to a medical table and to cover a portion of a C-arm as well as two sidewalls extending from a rotation end to a bottom end of the C-arm. The enclosure has a front wall extending between the sidewalls to enable a medical professional to move about the enclosure for accessing a patient on the table.

U.S. Pat. No. 9,855,178 to Rogers discloses a surgical drape system to cover patient support machinery, e.g., hoists, lifts, and slings, whether mobile, stationary, or otherwise configured as a floor-based or as an overhead support and/or lifting system. The drapes protect equipment from exposure to surgical biohazard waste, e.g., blood or body fluids, and enable the use of equipment not otherwise admittable to operating rooms due to an inability to render the equipment sterile. The drapes also enable the holding, lifting, and positioning of patients, while maintaining sterility during "prep" and surgical procedures.

Various C-arm machines currently available are equipped with walled plates or trays to place surgical instruments or store medical supplies, to make such available for use by medical practitioners during a procedure. Materials now used to cover surfaces of plates and trays during such procedures are flimsy and thus unable to provide a sterile environment for medical instruments, supplies, and surfaces. Also, during such procedures virtually all such flimsy material is quite often ripped, or become perforated or punctured, which causes a breach of sterile environments, surfaces, and fields, typically causing delays in surgical procedures, and raising concerns regarding patient infection.

A review of the prior art has not disclosed or even suggested a solution. Moreover, since sterile field breaches often occur with specialized C-arm machines equipped with C-arm covers and plates including "mini" C-arm plates, the present subject matter solves this problem by effectively fitting over C-arm covers and plates, to provide a radiolucent, protective barrier, and prevent breaches and contamination, for maintaining sterile fields.

SUMMARY OF THE INVENTION

The present subject matter is directed to a cover for use with a machine having a C-arm adapted to support a detector having a screen. The cover, designed to maintain a sterile field for the detector, includes a panel having at least three integral sides. Two sides are spaced-apart and disposed in parallel orientation. The cover also includes a pair of straps. One of the straps has an end portion fixed to one of the two parallel sides of the panel. The other strap has an end portion fixed to the other of the two parallel sides. The cover includes a hook-and-loop closure mechanism which has a hooked portion and a looped portion. Each strap has a fixed end portion and a free, opposite end portion. The free end portion of one strap includes the hooked portion and the free end portion of the other strap includes the looped portion. Each closure portion is sized, when the closure portions are engaged, to retain the panel against the detector, to maintain the sterile field.

BRIEF DESCRIPTION OF THE DRAWING FIGURES

FIG. 1 is a perspective view of an example of the present subject matter when used on a machine having a C-arm, where the C-arm supports a detector having a screen.

FIG. 2 presents a perspective view of an embodiment of the present subject matter.

FIG. 3 provides an upper perspective view of a detail of the present subject matter.

FIG. 4 presents an underside perspective view of a certain detail shown in FIG. 3.

DETAILED DESCRIPTION OF THE INVENTION

Figure 1:
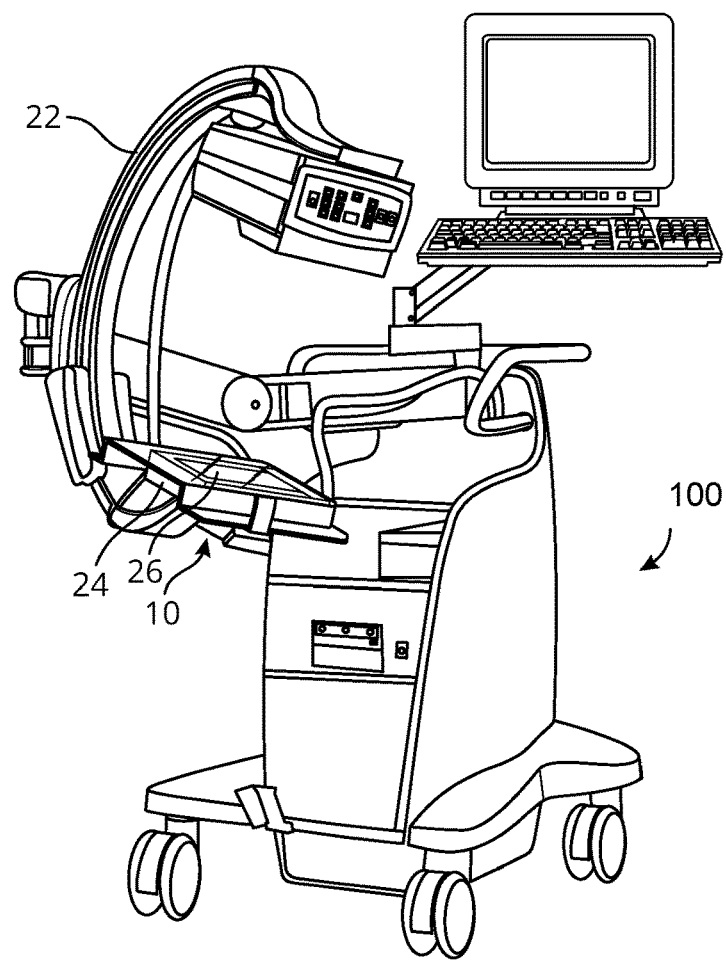

FIG. 1 a perspective view of an example of the present subject matter, a cover 10, shown in a preferred use on a machine or apparatus 100 having a C-arm 22, also referred to as a "mini" C-arm throughout this patent specification. The C-arm 22 shown is used to support a detector 24 (e.g., a flat plate detector) having a screen 26 (preferably planar).

Figure 2:
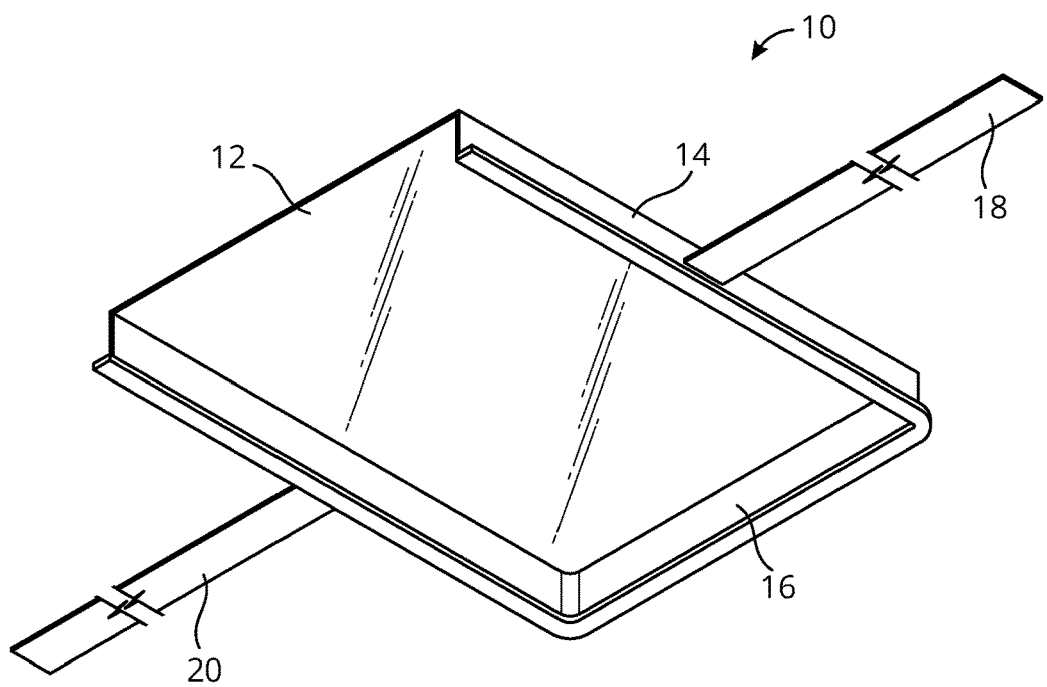
Figure 3:
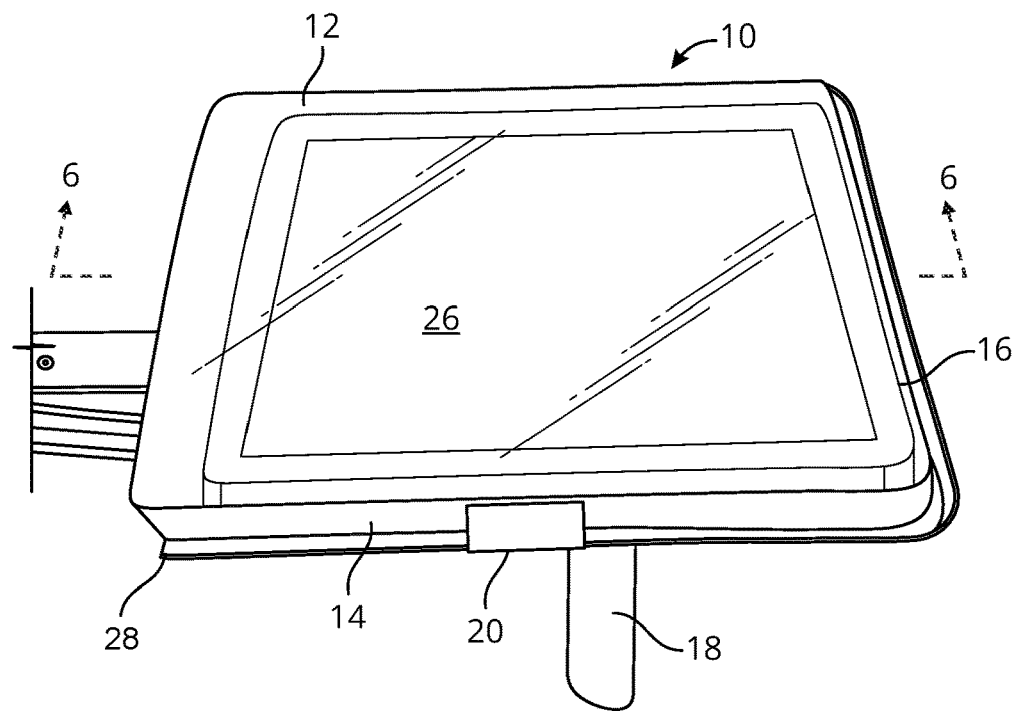
Figure 4:
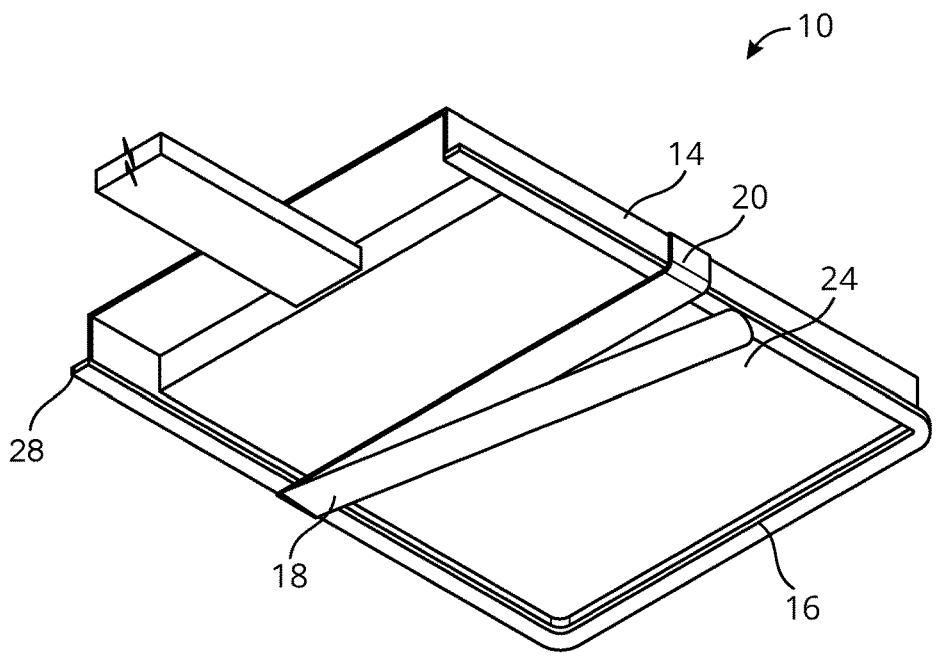
Figure 5:
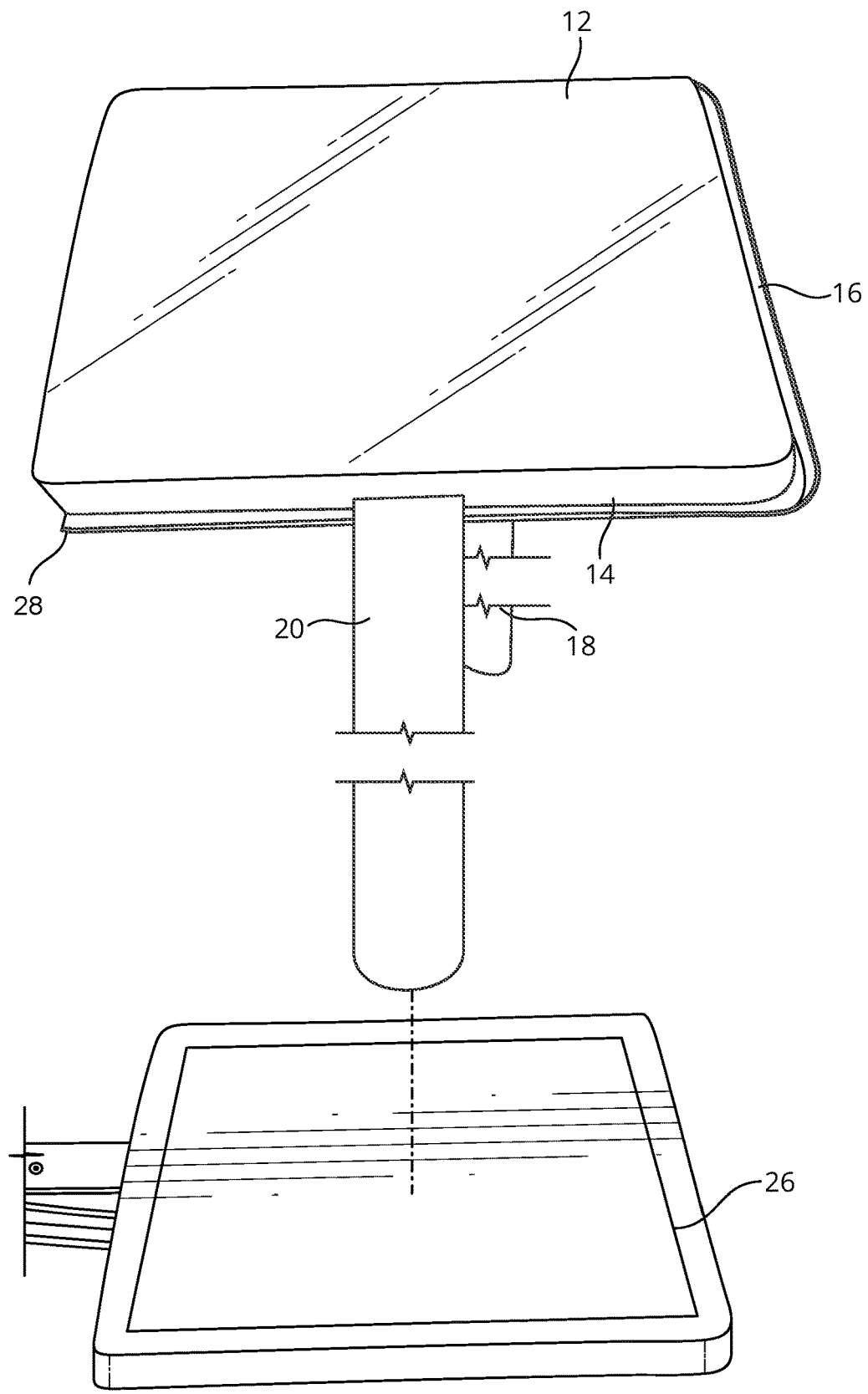
FIG. 5 is an exploded perspective view of the present subject matter by the screen.
Figure 6:
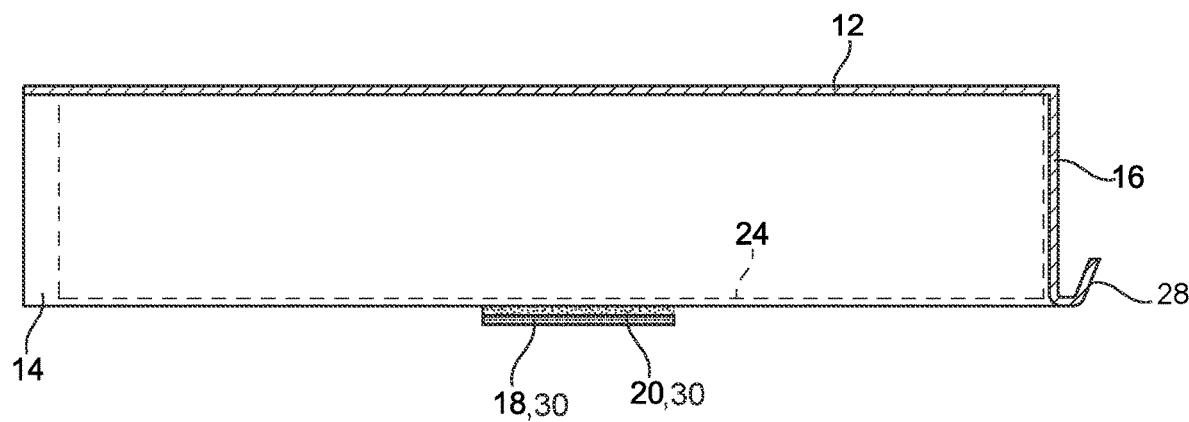
FIG. 6 is a cross-sectional and side-elevational view of the present subject matter, from a plane 6-6 disposed transverse to the C-arm detector screen depicted in FIG. 3.

Cover 10 (FIG. 2) includes a planar panel 12 (FIGS. 2-6), a pair of straps 18, 20 (FIG. 4) of predetermined length, and a hook-and-loop closure mechanism 30 (FIG. 6).

Panel 12 includes three integral sides 14 and 16. Two of the sides 14 are arranged parallel to each other and transverse to the third side 16 which is arranged between them.

Planar panel 12 is preferably rectangular (FIG. 2) and the three integral sides 14 and 16 are disposed transverse to the planar surface of panel 12. The parallel-spaced sides 14 have a predetermined length that is greater than the length of the third side 16.

The panel 12 of the current embodiment is dimensioned and configured, preferably to snugly engage and receive the detector 24 (FIG. 6) and to closely overlie screen 26. A lower edge margin of sides 14, 16 each include an integral upturned lip 28 (FIGS. 3-6).

Straps 18, 20 (FIG. 4) of the illustrated embodiment are elongated. Each strap 18, has a predetermined width and a predetermined length. Each strap 18, 20 is manufactured from a flexible, durable, and ecologically friendly material (e.g., nylon). One of the elongated straps (e.g., strap 18) has an end portion fixed to one (FIG. 2) of the spaced-apart longer sides 14 of panel 12 and the other elongated strap (e.g., strap 20) has an end portion fixed to the other (FIG. 5) longer side 14 (of the parallel-spaced sides 14). Each strap 18, 20 includes a portion of a hook-and-loop closure mechanism 30 secured to its free-end portion or along its entire length, with one strap (e.g., strap 18) having fixed to it one of the hook-and-loop closure mechanism portions and the other strap (e.g., strap 20) having fixed to it complimentary portion of closure mechanism 30.

The hook-and-loop closure mechanism 30 includes a hooked-closure portion and a looped-closure portion. The opposite end portion of one of the pair of straps 18 and 20 has the hooked-closure portion secured to it and the opposite end portion of the other one of the pair of straps 18 and 20 has the looped-closure portion secured to it (FIG. 6). In embodiments, the hooked-and-looped closure portions of the hook-and-loop closure mechanism 30 are dimensioned and configured, when brought into contact and engaged together (FIG. 6), to snugly retain the panel 12 against the detector 24 for maintaining the sterile field noted. Hook-and-loop closure mechanisms are well known. Please see, for example, U.S. Pat. No. 4,447,060 to Guinn; U.S. Pat. No. 4,488,323 to Colburn; and U.S. Pat. No. 4,498,615 to Johnson, each of which is hereby incorporated by reference in its entirety.

The cover 10 of the present subject matter can be made from flexible and durable materials including but not limited to polyurethane, high-density ethylene, high-density polypropylene, and silicone-based polymeric materials. Cover 10, preferably transparent or translucent, is made by 3-D printing, molded, stamped, or vacuum-based processes.

Illustrated and described throughout this patent application is an example of a protective cover sized, adapted, and configured for maintaining a sterile field for a "mini" C-arm flat-plate detector. While the present subject matter has been described with reference to an illustrated exemplary embodiment, the present subject matter is not limited to the embodiment described herein. On the contrary, many alternatives, changes, and/or modifications shall become apparent to a person of ordinary skill in the art ("POSITA") after this application is read and its associated figures reviewed. Therefore, all alternatives, changes, and/or modifications are to be considered as forming a part of the present subject matter insofar as they fall within the spirit and scope of the claims.

What is claimed is:

1. A cover for use with an apparatus (100) having a C-arm (22), wherein the C-arm (22) is adapted and configured for supporting a detector (24) having a screen (26), wherein the cover (10) is configured for maintaining a sterile field for the detector (24), wherein the cover (10) comprises:

a panel (12) defining at least three integral sides (14, 16), wherein two sides (14) of the at least three integral sides (14, 16) are disposed transverse to the panel (12) and are parallel-spaced-apart from each other, wherein the panel (12) is dimensioned and configured to receive the detector (24) and to overlie on the screen (26);

a pair of straps (18, 20), wherein a first strap (18) of the pair of straps (18, 20) has one end portion affixed to a first side (14) of the two parallel-spaced-apart sides (14) of the at least three integral sides (14, 16), wherein a second strap (20) of the pair of straps (18, 20) has one end portion affixed to a second side (14) of the two parallel-spaced-apart sides (14) of the at least three integral sides (14, 16), wherein the first strap (18) of the pair of straps (18, 20) has an opposite end portion, wherein the second strap (20) of the pair of straps (18, 20) has an opposite end portion; and a hook-and-loop closure mechanism (30) comprising a hooked-closure portion and a looped-closure portion, wherein a first one of the opposite-end portions of the first and second straps (18, 20) includes the hooked-closure portion affixed thereto, wherein a second one of the opposite-end portions of the first and second straps (18, 20) includes the looped-closure portion affixed thereto, wherein each of the hooked-and-looped closure portions is dimensioned and configured when engaged together to snugly retain the panel (12) against the detector (24), for maintaining the sterile field.

2. The cover of claim 1, wherein the detector (24) is a flat plate detector.

3. The cover of claim 1, wherein the panel (12) is planar.

4. The cover of claim 1, wherein the pair of straps (18, 20) are each elongated.

5. The cover of claim 1, wherein the panel (12) is rectangular, wherein all of the at least three integral sides (14, 16) are disposed transverse to the panel (12), wherein two sides (14) of the at least three integral sides (14, 16) are spaced in parallel orientation in relation to a third side (16) of the at least three integral sides (14, 16) disposed therebetween.

6. The cover of claim 1, wherein the panel (12) is rectangular, wherein all of the at least three integral sides (14, 16) are disposed transverse to the panel (12), wherein two sides (14) of the at least three integral sides (14, 16) are spaced in parallel orientation in relation to a third side (16) of the at least three integral sides (14, 16) disposed therebetween, and wherein the cover (10) is made by a 3-D printing, a molded, a stamped, or a vacuum process.

7. The cover of claim 5, wherein the detector (24) is a flat plate detector.

8. The cover of claim 5, wherein the panel (12) is planar.

9. The cover of claim 5, wherein the pair of straps (18, 20) are each elongated.

* * * * *